(12) United States Patent
Suzuki et al.

(10) Patent No.: US 8,566,691 B2
(45) Date of Patent: Oct. 22, 2013

(54) ANALYZER

(75) Inventors: Takayuki Suzuki, Tokyo (JP); Shinjirou Kiyono, Tokyo (JP); Ryuji Chiba, Tokyo (JP)

(73) Assignee: Yokogawa Electric Corporation, Tokyo (JP)

(*) Notice: Subject to any disclaimer, the term of this patent is extended or adjusted under 35 U.S.C. 154(b) by 337 days.

(21) Appl. No.: 13/110,321

(22) Filed: May 18, 2011

(65) Prior Publication Data

US 2011/0289374 A1    Nov. 24, 2011

(30) Foreign Application Priority Data

May 21, 2010   (JP) .................................. 2010-116891

(51) Int. Cl.
   *G06F 7/02*     (2006.01)
   *G06F 11/00*    (2006.01)
   *G11C 29/00*    (2006.01)

(52) U.S. Cl.
   USPC ............. 714/819; 714/5.11; 714/6.1; 714/13; 714/51; 714/57; 714/763

(58) Field of Classification Search
   USPC ........ 714/2, 4.1, 4.11, 4.12, 4.2, 4.3, 4.4, 4.5, 714/5.1, 5.11, 6.1, 6.3, 10, 13, 25, 32, 33, 714/37, 47.1, 51, 57, 724, 741, 742, 763, 714/811, 819
   See application file for complete search history.

(56) References Cited

U.S. PATENT DOCUMENTS

| | | | |
|---|---|---|---|
| 8,065,564 B2* | 11/2011 | Nakatani et al. ................. | 714/37 |
| 2006/0174155 A1* | 8/2006 | Mansell ............................ | 714/5 |
| 2012/0030504 A1* | 2/2012 | Nishiyama et al. .......... | 714/4.11 |

FOREIGN PATENT DOCUMENTS

JP         2002-90369 A       3/2002

* cited by examiner

*Primary Examiner* — Christine Tu
(74) *Attorney, Agent, or Firm* — Sughrue Mion, PLLC

(57) ABSTRACT

An analyzer may include a body housing having a first ID, a first measurement module having a second ID that is different from the first ID, the first measurement module being releasably attachable to the body housing, a first memory in the body housing, the first memory being configured to store the first ID, first setting data and first correction data, a second memory in the first measurement module, the second memory being configured to store the second ID, second setting data and second correction data, a first CPU in the body housing, the first CPU being configured to detect the first measurement module having the second ID, and a first data transmission unit in the body housing, the first data transmission unit being configured to transmit the first setting data and the first correction data to the second memory.

20 Claims, 6 Drawing Sheets

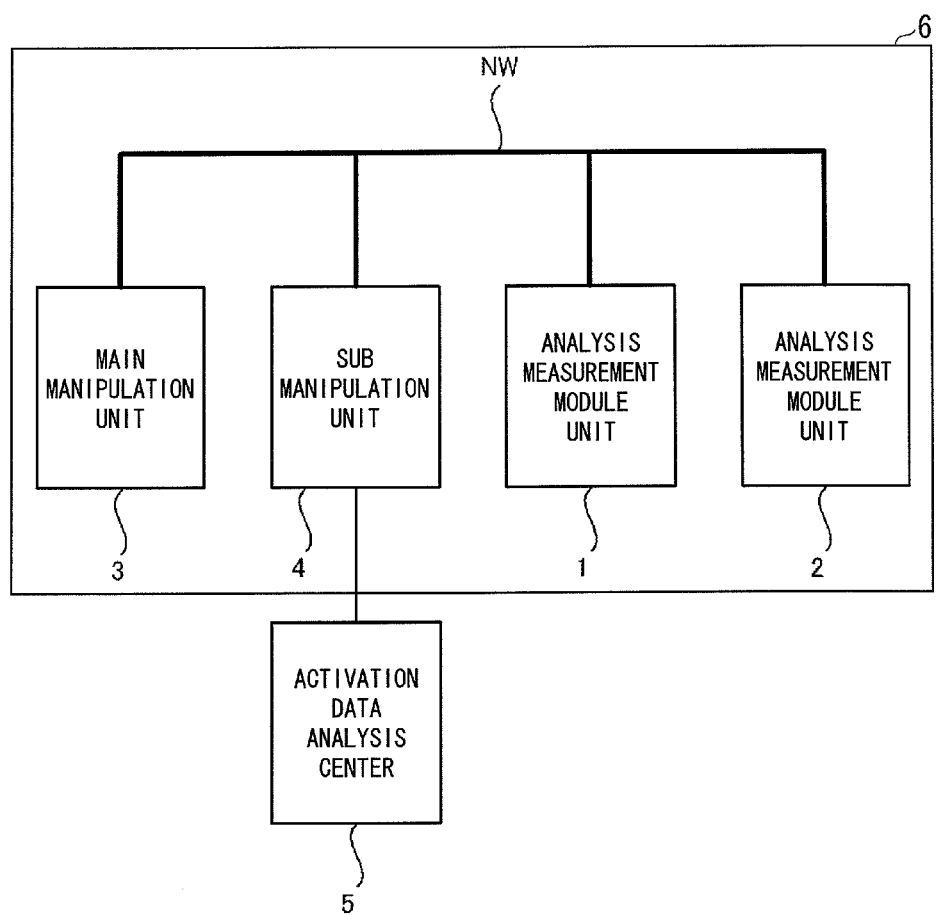

ANALYZER

BACKGROUND OF THE INVENTION

1. Field of the Invention

The present invention relates to an analyzer. Specifically, the present invention relates to a downsizing of the analyzer that has a measurement module structure and performs backup of various data.

Priority is claimed on Japanese Patent Application No. 2010-116891, filed May 21, 2010, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

Japanese Unexamined Patent Application, First Publication No. 2002-090369 discloses an analyzer including a plurality of analysis measurement module units, a main manipulation unit and a sub manipulation unit, which are connected to each other through a network.

FIG. 6 is a block diagram illustrating an example of the analyzer disclosed in Japanese Unexamined Patent Application, First Publication No. 2002-090369. The analyzer 6 includes an analysis measurement module unit 1, an analysis measurement module 2, a main manipulation unit 3, a sub manipulation unit 4, and a network NW. The analysis measurement module unit 1, the analysis measurement module 2, the main manipulation unit 3, and the sub manipulation unit 4 are connected to each other through the network NW. The sub manipulation unit 4 includes database for backup. The analysis measurement module units 1 and 2 include a code for confirming a safety of the database after a recovery.

The analysis measurement module units 1 and 2 include a dispensing structure, a reagent dispensing structure, a stirrer structure, a multiple wavelength photometer, and a washing structure. The dispensing structure is for dispensing a specimen to a reaction container. The reagent dispensing structure is for dispensing a reagent to the reaction container. The stirrer structure is for stirring a mixed liquid in the reaction container. The multiple wavelength photometer measures an absorbance of the mixed liquid in the reaction container. The washing structure is for washing the used reaction container.

The analysis measurement module units 1 and 2 mix the specimen with the reagent in the reaction container. Then, the multiple wavelength photometer measures the absorbance of the mixed liquid by using a wavelength based on each analysis item. Thereby, the analysis measurement module units 1 and 2 analyze the specimen.

The main manipulation unit 3 and the sub manipulation unit 4 are man-machine interfaces with the analysis measurement module units 1 and 2. The main manipulation unit 3 and the sub manipulation unit 4 are for inputting a requested analysis item corresponding to the specimen, instructing a start/stop of analysis, displaying contents on a screen when the analysis measurement module units 1 and 2 output an alarm, and so on.

If the main manipulation unit 3 cannot perform its process by some abnormality, the sub manipulation unit 4 is used as a manipulation unit instead of the main manipulation unit 3. Settings of the sub manipulation unit 4 are changed so as to be used as the manipulation unit. While performing the settings of the sub manipulation unit 4, the processes such as a specimen analysis by the analysis measurement module units 1 and 2 are stopped. The analysis measurement module units 1 and 2 stop the processes while performing the settings of the sub manipulation unit 4. Thereby, the analyzer can be used normally and reliability of the analyzer can be increased.

Either the main manipulation unit 3 or the sub manipulation unit 4 may be a service processor. In the example of FIG. 6, the sub manipulation unit 4 is the service processor and is connected to an activation data analysis center 5 through a public line etc. The service processor stores periodic data and operational status data. The periodic data is necessary in performing a periodic inspection on the analysis measurement module units 1 and 2. The operational status data is, for example, trouble data of the analysis measurement module units 1 and 2. The service processor transmits the operational status data of the analysis measurement module units 1 and 2 to the activation data analysis center 5 through the public line and the like. The service processor transmits the trouble data showing that some abnormality occurs in the main manipulation unit 3 to the activation data analysis center 5 through the public line and the like.

The service processor determines that a lifetime of parts comes to the end based on an overall conduction time of the analyzer. The result of the determination is transmitted to the activation data analysis center 5. The activation data analysis center 5 can recommend an exchange of parts to a user based on the result of the determination for a preventive maintenance. The parts are, for example, a hard disk or a flash ROM storing the database.

The analysis measurement module units 1 and 2 calculates a concentration of the specimen from the absorbance and a variation in the absorbance of the mixed liquid that are measured based on a standard curve for converting to the concentration and an activity value. The data of the standard curve is varied based on a state of the analyzer and the reagent. Therefore, the data of the standard curve that has passed a prescribed time period cannot be used. Also, it is important to coordinate the data of the standard curve with the reagent. In the analysis measurement module units 1 and 2, it is necessary to recognize the data of the standard curve and the state of the reagent properly.

When storage storing the database has a problem and the database is restructured after the storage is repaired, if the database before the problem can be restored, it is not necessary to perform a reagent registration operation and a calibration operation. The time for restructuring the database can be shortened by performing a mirroring of the database anytime so as to enable a recovery. The mirroring should be performed in the existing system without adding an additional server to the system.

The database is included in either the main manipulation unit 3, the analysis measurement module units 1 or 2. In every case, the analysis measurement module units 1 and 2 transmit a result of a measurement and data of a used amount of the reagent to a unit including the database and the sub manipulation unit 4 that is the service processor.

The sub manipulation unit 4 structures the whole database or a selected part of the database inside the sub manipulation unit 4 by using the same process as the main manipulation unit 3. The database in the main manipulation unit 3 is mirrored to the sub manipulation unit 4 so as to coordinate the data when the communication load is small such as when the analyzer is started/reset.

It is necessary to confirm that the data has no error when restored. A timestamp is attached to the data transmitted from the main manipulation unit 3 to the sub manipulation unit 4 at the timing of performing the communication to specify the timing when the error occurs. The timestamp is, for example, a check digit to maintain the reliability of the data. The analyzer including the database stores the latest timestamp in a nonvolatile memory or the like. The time data stored in each unit does not correspond to the other units. To correct the gap in the time data, the timestamp includes data such as the number of times of the communications.

The timestamp data is the data when the communication is performed. Data, which is generated after the communication and is not sent to the database for backup, is also attached to the timestamp data stored in the nonvolatile memory of the analyzer so as to determine whether or not the reagent is dispensed after the communication and whether or not a new standard curve is generated after the communication.

The software in the analyzer recognizes that the operation of restoring the database is performed. The following operations are performed by comparing the timestamp.

If the timestamp of the database for backup corresponds to the timestamp of the analyzer, then it turns out that the storage storing the database of the analyzer had broken down after the database for backup is normally updated. In this case, the database for backup is reliable, and the database for backup is copied to a storage storing a new database of the analyzer. Whether or not new data is generated after the communication is confirmed based on the timestamp data stored in the nonvolatile memory of the analyzer. If there is new data, the new data is transmitted to the database to update the database.

If the timestamp of the database for backup is newer than the timestamp of the analyzer, it is determined that an error occurs in the process of the software and the database for backup cannot be copied to a new storage in the analyzer. In this case, it is assumed that the error is based not on the error in hardware of the storage storing the database but on the error in an operation of the software. Therefore, error information indicates as such.

If the timestamp of the database for backup is older than the timestamp of the analyzer, then there is a capability that the storage has broken out after the analyzer cannot perform a communication, a trouble has occurred on the network, and a trouble has occurred in the database for backup.

It is difficult to store all operations while the timestamp has a gap to the nonvolatile memory of the analyzer, the user is encouraged to correct the consumption of the reagent and the generated data of the standard curve while the timestamp has a gap.

By the configuration of FIG. 6 in accordance with the related art, the database can be backed up while the operation unit is redundant. It is difficult to downsize the analyzer.

SUMMARY

An analyzer may include a body housing having a first ID, a first measurement module having a second ID that is different from the first ID, the first measurement module being releasably attachable to the body housing, a first memory in the body housing, the first memory being configured to store the first ID, first setting data and first correction data, a second memory in the first measurement module, the second memory being configured to store the second ID, second setting data and second correction data, a first CPU in the body housing, the first CPU being configured to detect the first measurement module having the second ID, and a first data transmission unit in the body housing, the first data transmission unit being configured to transmit the first setting data and the first correction data to the second memory.

An analyzer may include a body housing having a first ID, a first measurement module having a second ID, the first measurement module being releasably attachable to the body housing, a first memory in the body housing, the first memory being configured to store the first ID, a third ID that is different from the first ID, first setting data and first correction data, a second memory in the first measurement module, the second memory being configured to store the second ID, a fourth ID that is different from the second ID, second setting data and second correction data, a first CPU in the body housing, the first CPU being configured to determine whether or not the second ID is different from the third ID, and a first data transmission unit in the body housing, the first data transmission unit being configured to transmit the first setting data and the first correction data to the second memory if the first CPU determines that the second ID is different from the third ID.

An analyzing method may include determining whether or not a first ID registered in a first memory of a body unit is different from a second ID allocated to a first measurement module, and transmitting first setting data and first correction data stored in the first memory to a second memory of the first measurement module if it is determined that the first ID is different from the second ID.

BRIEF DESCRIPTION OF THE DRAWINGS

The above features and advantages of the present invention will be more apparent from the following description of certain preferred embodiments taken in conjunction with the accompanying drawings, in which:

FIG. 6 is a block diagram illustrating an example of an analyzer in accordance with a related art.

DETAILED DESCRIPTION OF THE PREFERRED EMBODIMENTS

Figure 1:
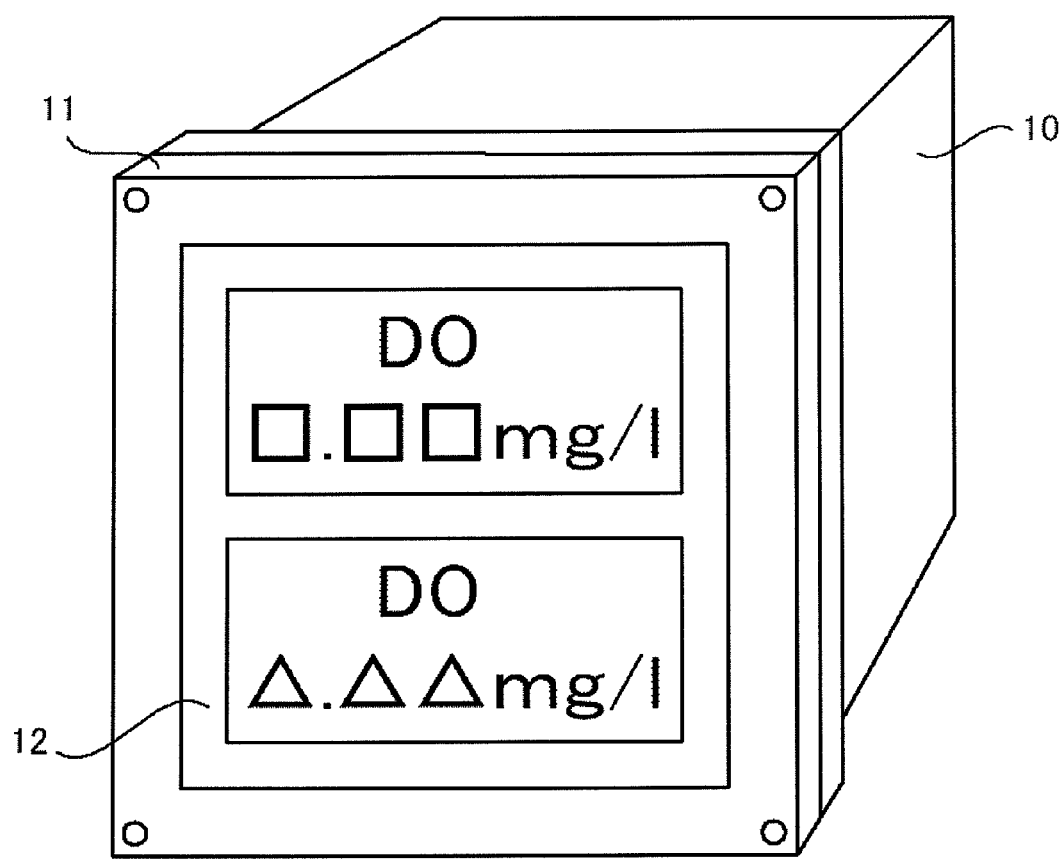
FIG. 1 is a view illustrating an outline of an analyzer in accordance with a first preferred embodiment of the present invention.

The present invention will be now described herein with reference to illustrative embodiments. Those skilled in the art will recognize that many alternative embodiments can be accomplished using the teaching of the present invention and that the present invention is not limited to the embodiments illustrated herein for explanatory purposes.

An analyzer may include a body housing having a first ID, a first measurement module having a second ID that is different from the first ID, the first measurement module being releasably attachable to the body housing, a first memory in the body housing, the first memory being configured to store the first ID, first setting data and first correction data, a second memory in the first measurement module, the second memory being configured to store the second ID, second setting data and second correction data, a first CPU in the body housing, the first CPU being configured to detect the first measurement module having the second ID, and a first data transmission unit in the body housing, the first data transmission unit being configured to transmit the first setting data and the first correction data to the second memory.

The analyzer may further include a second CPU in the first measurement module, the second CPU being configured to detect the body housing having the first ID, and a second data transmission unit in the first measurement module, the second data transmission unit being configured to transmit the second setting data and the second correction data to the first memory.

The analyzer may further include a display unit in a front side of the body housing, the display unit including a touch panel.

The analyzer may be configured to connect to an instrument panel room through a two-wire transmission path.

The analyzer may be configured to connect to an instrument panel room through a four-wire transmission path.

The analyzer may further include a second measurement module having a third ID that is different from the first ID and the second ID, the second measurement module being releasably attachable to the body housing, a third memory in the second measurement module, the third memory being configured to store the third ID, third setting data and third correction data. The first CPU may be configured to detect the second measurement module having the third ID, and the first data transmission unit may be configured to transmit the first setting data and the first correction data to the third memory.

The analyzer may further include a third CPU in the second measurement module, the third CPU being configured to detect the body housing having the first ID, and the first measurement module having the second ID, and a third data transmission unit in the second measurement module, the third data transmission unit being configured to transmit the third setting data and the third correction data to the first memory and the second memory.

The second CPU may be configured to detect the second measurement module having the third ID, and the second data transmission unit is configured to transmit the second setting data and the second correction data to the third memory.

An analyzer may include a body housing having a first ID, a first measurement module having a second ID, the first measurement module being releasably attachable to the body housing, a first memory in the body housing, the first memory being configured to store the first ID, a third ID that is different from the first ID, first setting data and first correction data, a second memory in the first measurement module, the second memory being configured to store the second ID, a fourth ID that is different from the second ID, second setting data and second correction data, a first CPU in the body housing, the first CPU being configured to determine whether or not the second ID is different from the third ID, and a first data transmission unit in the body housing, the first data transmission unit being configured to transmit the first setting data and the first correction data to the second memory if the first CPU determines that the second ID is different from the third ID.

The first memory may be configured to store the second ID after the first setting data and the first correction data are transmitted to the second memory.

The analyzer may further include a second CPU in the first measurement module, the second CPU being configured to determine whether or not the first ID is different from the fourth ID, and a second data transmission unit in the first measurement module, the second data transmission unit being configured to transmit the second setting data and the second correction data to the first memory if the second CPU determines that the first ID is different from the fourth ID.

The analyzer may further include a display unit in a front side of the body housing, the display unit including a touch panel.

The analyzer may be configured to connect to an instrument panel room through a two-wire transmission path.

The analyzer may be configured to connect to an instrument panel room through a four-wire transmission path.

An analyzing method may include determining whether or not a first ID registered in a first memory of a body unit is different from a second ID allocated to a first measurement module, and transmitting first setting data and first correction data stored in the first memory to a second memory of the first measurement module if it is determined that the first ID is different from the second ID.

The analyzing method may further include determining whether or not a third ID registered in the second memory is different from a fourth ID allocated to the body unit, and transmitting second setting data and second correction data stored in the second memory to the first memory if it is determined that the third ID is different from the fourth ID.

The analyzing method may further include transmitting data to an instrument panel room through a two-wire transmission path.

The analyzing method may further include transmitting data to an instrument panel room through a four-wire transmission path.

The analyzing method may further include determining whether or not a fifth ID registered in the second memory is different from a sixth ID allocated to a second measurement module, and transmitting third setting data and third correction data stored in the second memory to a third memory of the second measurement module if it is determined that the fifth ID is different from the sixth ID.

The analyzing method may further include registering the second ID in the first memory after the first setting data and the first correction data are transmitted to the second memory.

The size of the analyzer in accordance with preferred embodiments of the present invention is small. The analyzer has a modular structure in which the analyzer can be used in the state before an exchange, so that it is not necessary to repeat a setting and a correction even if a body housing and an analysis measurement module are exchanged.

In the analyzer in accordance with preferred embodiments of the present invention, setting data and correction data are backed up when the body housing and the analysis measurement module are exchanged. Thereby, the size of the analyzer becomes small. The analyzer has a modular structure in which the analyzer can be used in the state before the exchange, so that it is not necessary to repeat a setting and a correction.

A first preferred embodiment of the present invention will be described by using figures. FIG. 1 is a view illustrating an outline of the analyzer in accordance with the first preferred embodiment of the present invention. The analyzer includes a body housing 10 that is formed as a box having a waterproof structure. The front of the body housing 10 is opening. A front panel 11 is attached to the front of the body housing 10 by using screws so as to achieve the waterproof structure. A display unit 12 is disposed in front of the front panel 11 so as to be operated from the front. The display unit 12 includes a touch panel and has a waterproof structure.

Figure 2:
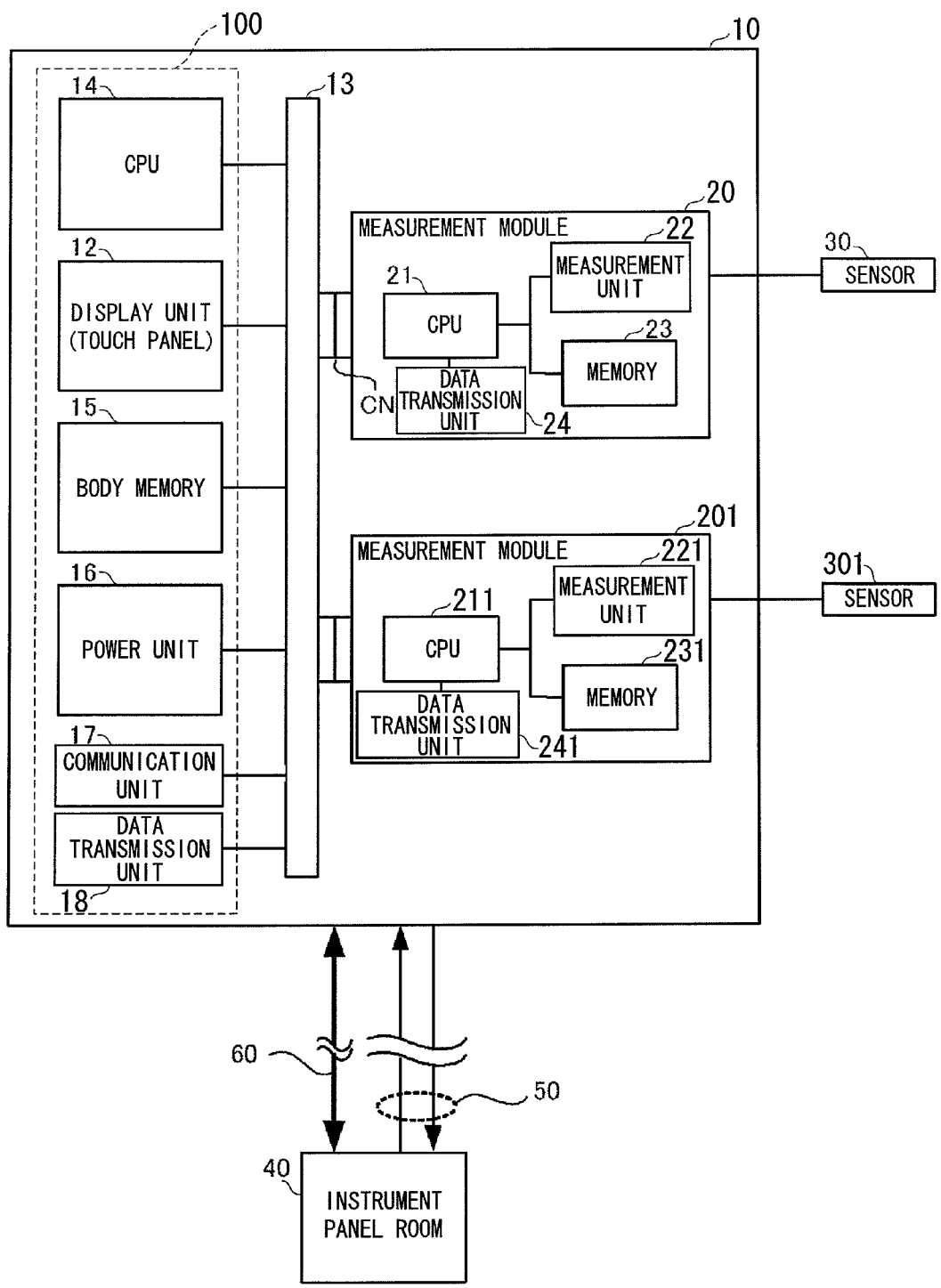
FIG. 2 is a block diagram illustrating a configuration of the analyzer in accordance with the first preferred embodiment of the present invention.

FIG. 2 is a block diagram illustrating a configuration of the analyzer in accordance with the first preferred embodiment of the present invention. The body housing 10 includes a printed board 13, a body circuit 100, and at least one of measurement modules 20 and 201. The body circuit 100 is formed on the printed board 13. At least one of the measurement modules 20 and 201 are disposed on the printed board 13 through connectors CN. The measurement modules 20 and 201 are exchangeable. FIG. 2 illustrates an example in which two measurement modules 20 and 201 are disposed on the printed board 13. The number of the measurement modules is not limited to two, but may be any arbitrary number. The measurement module 20 is connected to a sensor 30. The measurement module 201 is connected to a sensor 301.

The body circuit 100 includes the display unit 12, a CPU 14, a body memory 15, a power unit 16, a communication unit 17, and a data transmission unit 18.

The CPU 14 controls whole of the analyzer.

Figure 3:
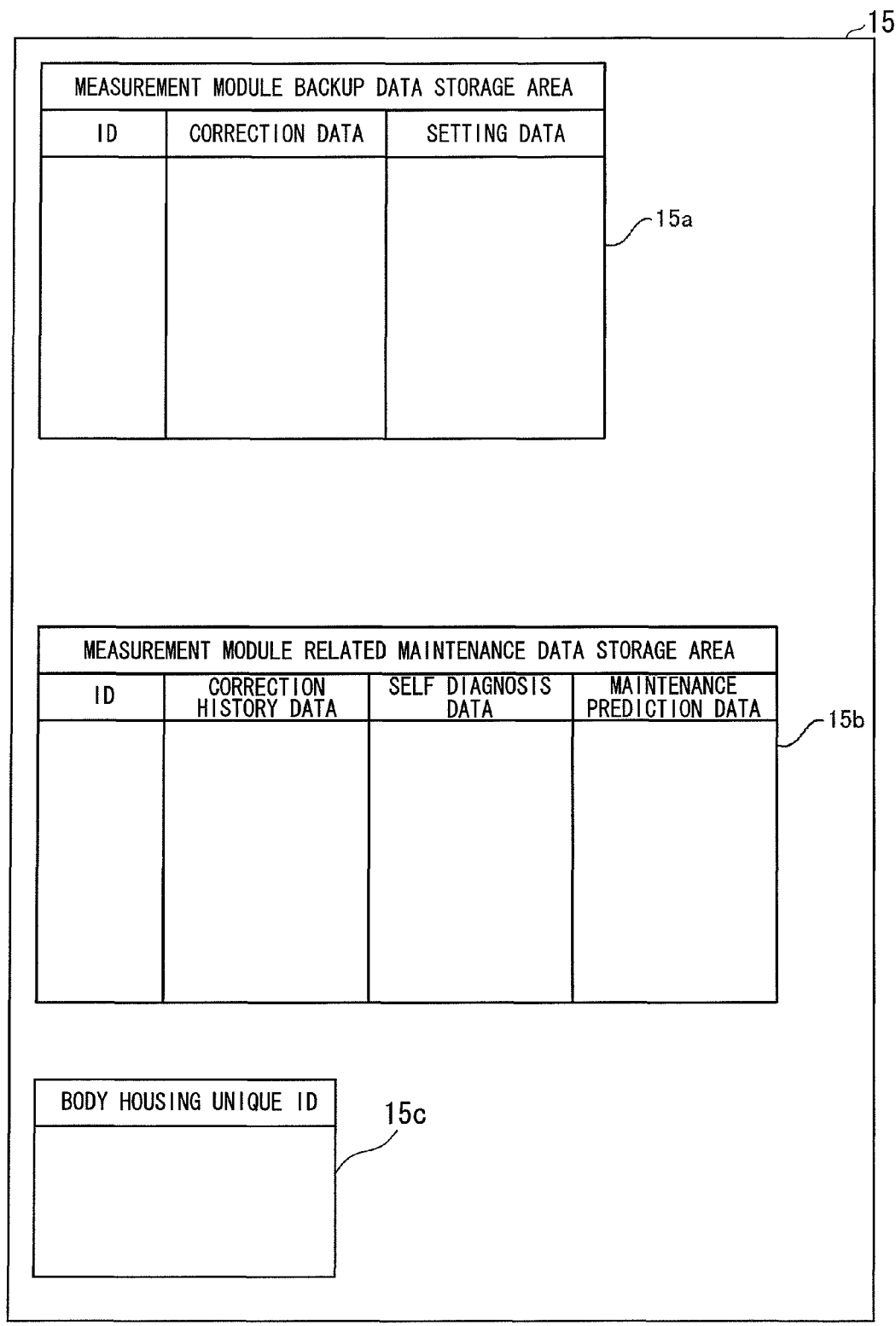
FIG. 3 is a view illustrating a configuration of a body memory of the analyzer in accordance with the first preferred embodiment of the present invention.

FIG. 3 is a view illustrating a configuration of the body memory 15.

As illustrated in FIG. 3, the body memory 15 includes a measurement module backup data storage area 15a, a measurement module related maintenance data storage area 15b, and an area storing a body housing unique ID 15c. The measurement module backup data storage area 15a includes an ID specific to the measurement module 20/201, correction data, and setting data. The measurement module related maintenance data storage area 15b includes an ID specific to the measurement module 20/201, correction history data, self diagnosis data of the sensor 30/301, and maintenance prediction data.

The power unit 16 generates a prescribed power voltage that is needed in driving the body circuit 100 and the measurement module 20/201. The power voltage is supplied to each unit through the printed board 13.

The communication unit 17 transmits/receives various signals between the analyzer and an instrument panel room 40 through a two-wire transmission path 50 and a digital bus 60. The digital bus 60 accepts digital communication standards such as HART communication protocol, FOUNDATION™ fieldbus, and PROFIBUS™.

When the analyzer and the instrument panel room 40 are connected through the two-wire transmission path 50, then the power voltage is transmitted from the instrument panel room 40 to the power unit 16 through the two-wire transmission path 50, and measurement data of the measurement module 20/201 is transmitted to the instrument panel room 40 through the two-wire transmission path 50.

When the analyzer and the instrument panel room 40 are connected through the digital bus 60, then the measurement data of the measurement module 20/201 is transmitted to the instrument panel room 40, and maintenance data such as the self diagnosis data and the maintenance prediction data stored in the measurement module related maintenance data storage area 15b of the body memory 15 is also transmitted to the instrument panel room 40.

The measurement module 20 includes a CPU 21, a measurement unit 22, a memory 23, and a data transmission unit 24. The measurement module 20 is connected to the sensor 30 disposed outside of the analyzer.

Also, the measurement module 201 includes a CPU 211, a measurement unit 221, a memory 231, and a data transmission unit 241. The measurement module 201 is connected to the sensor 301 disposed outside of the analyzer.

The measurement module 20/201 is configured for each usage such as measuring a pH/ORP (oxidation reduction potential), measuring an electric conductivity, measuring an electromagnetic conductivity, and measuring a dissolved oxygen. Measurement of an intended purpose can be performed by connecting the measurement module 20/201 to the sensor 30/301 suitable for the purpose of the measurement.

The body housing 10 and the measurement module 20/201 included in the analyzer is set as follows:

(1) A corresponding unique ID is allocated to each of the body housing 10, and the measurement modules 20 and 201.

(2) Each of the body memory 15 of the body housing 10, the memory 23 of the measurement module 20, and the memory 231 of the measurement module 201 registers/stores the corresponding unique ID.

(3) Each of the body memory 15 of the body housing 10, the memory 23 of the measurement module 20, and the memory 231 of the measurement module 201 stores setting data and correction data that are desired to be backed up.

Figure 4:
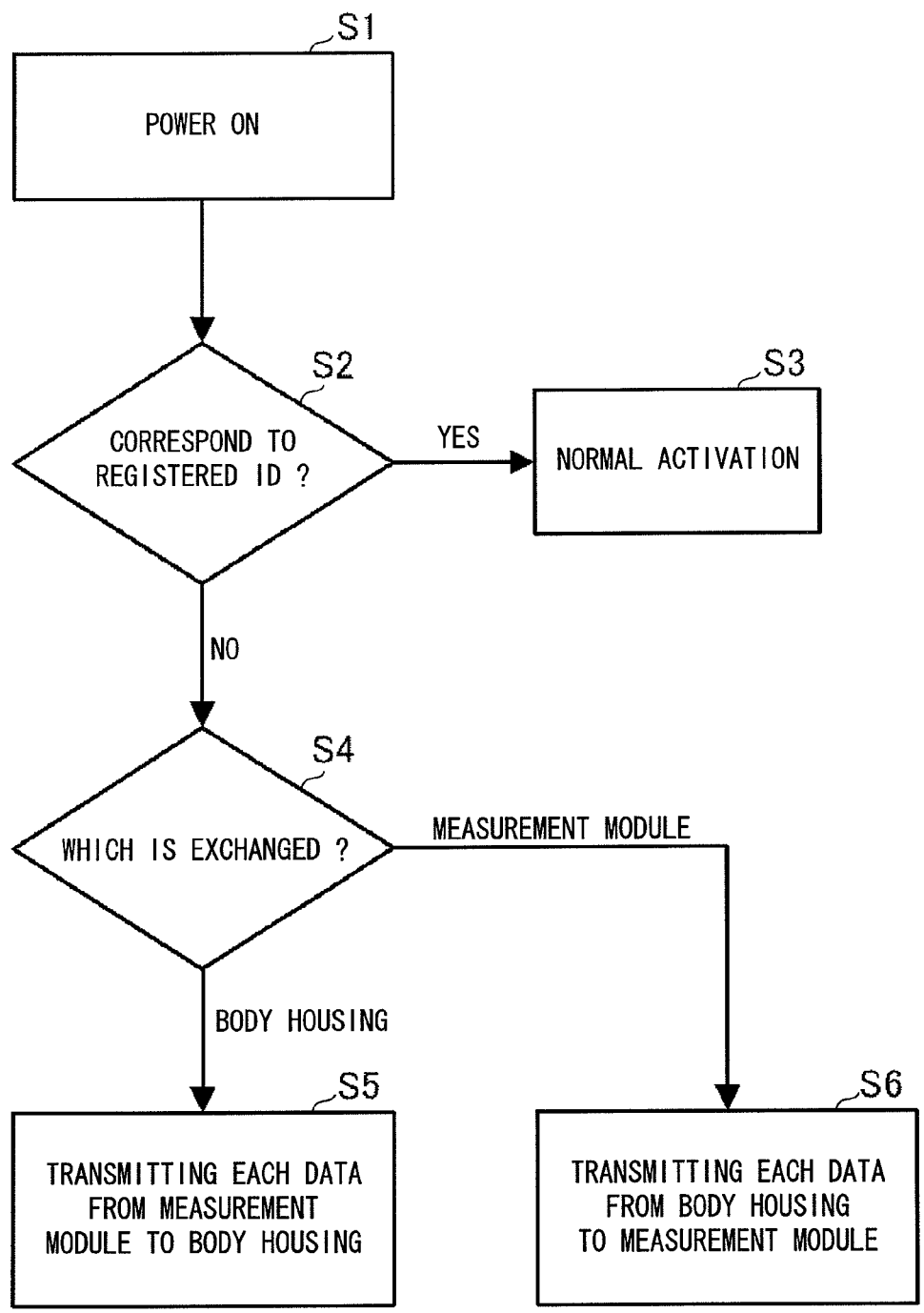
FIG. 4 is a flowchart illustrating an operation of the analyzer when powered on in accordance with the first preferred embodiment of the present invention.

FIG. 4 is a flowchart illustrating an operation of the analyzer when powered on.

In Step S1, the analyzer is powered on.

In Step S2, the CPU 14 in the body circuit 100 asks the CPU 21 in the measurement module 20 of a specific ID. Then, the CPU 14 determines whether or not the specific ID corresponds to a registered ID that is registered beforehand. Also, the CPU 21 in the measurement module 20 asks the CPU 14 in the body circuit 100 of a specific ID. Then, the CPU 21 determines whether or not the specific ID corresponds to a registered ID that is registered beforehand.

If it is determined that the specific ID corresponds to the registered ID by both the CPU 14 and the CPU 21, then the process goes to Step S3 to be operated normally.

If a combination of the body housing 10 and the measurement module 20/201 is changed, then at least one of the specific ID does not correspond to the registered ID and the process goes to Step S4 that is a backup mode.

Figure 5:
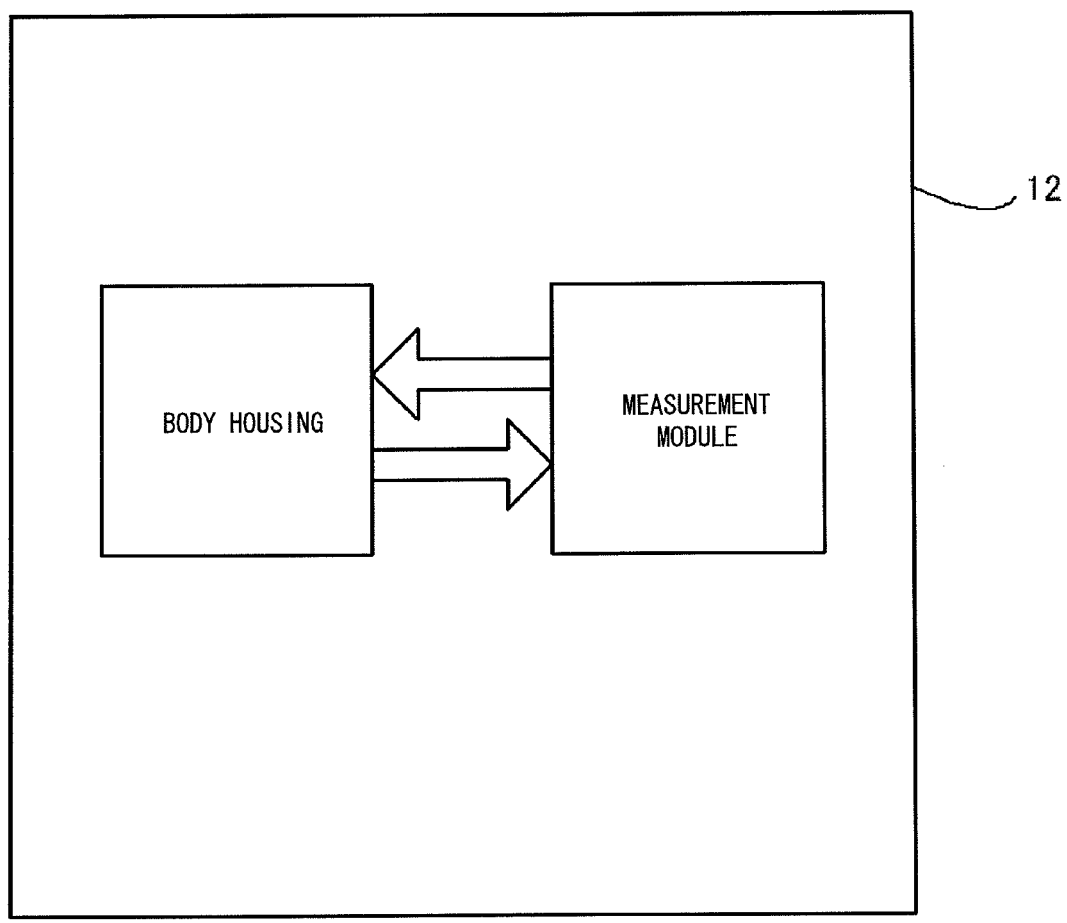
FIG. 5 is a view illustrating an example of a backup screen in the display unit of the analyzer in accordance with the first preferred embodiment of the present invention.

FIG. 5 is a view illustrating an example of a backup screen in the display unit 12. The backup screen displays a box of the body housing and a box of the measurement module.

In Step S4, the display screen of the display unit 12 is changed to the backup screen as illustrated in FIG. 5. The operator recognizes the changed contents of the combination of the body housing 10 and the measurement module 20/201. The operator can select a target of backup of the setting data and the correction data from the body housing and the measurement module in the backup screen of FIG. 5.

If the body housing 10 has been exchanged, the operator clicks the displayed box of the body housing and the process goes to Step S5. In Step S5, the data transmission unit 24 of the measurement module 20 transmits the setting data and the correction data that are desired to back up from the memory 23 of the measurement module 20 to the body memory 15 of the body housing 10. Thereby, the setting data and the correction data of the body memory 15 are overwritten and updated to perform the backup.

If the measurement module 20 has been exchanged, the operator clicks the displayed box of the measurement module and the process goes to Step S6. In Step S6, the data transmission unit 18 of the body housing 10 transmits the setting data and the correction data that are desired to back up from the body memory 15 of the body housing 10 to the memory 23 of the measurement module 20. Thereby, the setting data and the correction data of the memory 23 of the measurement module 20 are overwritten and updated to perform the backup.

By using the configuration described above, the setting data and the correction data can be backed up and the measurement item can be changed flexibly, only by exchanging the measurement module and the sensor/detector that are combined with a transmission device according to the measurement purpose. Thereby, an analyzer having a large amount of freedom can be attained.

Two sensors that are the same kind can be connected to a two-wire transmission device. Thereby, one transmission device can analyze two sensors, and small cost and small space can be attained.

The two-wire transmission device includes the display unit 12 with touch panel. Thereby, various settings and change of display can be performed on the display screen, and an operability of the operator at the field can be improved largely.

The maintenance data such as the correction history data and the self diagnosis data of the measurement module can be transmitted to the instrument panel room and the like through the digital bus if necessary. Thereby, suitable maintenance can be operated effectively.

By combining the self diagnosis function of the sensor, future maintenance and the time for correction can be predicted.

In the first preferred embodiment of the present invention described above, the transmission unit includes the two-wire transmission path that performs the power supply and the signal transmission by using two signal paths commonly. But the present invention is not limited to the above-described configuration. For example, the power supply and the signal transmission may be performed separately by using a four-wire transmission path that includes two independent signal paths. Thereby, a format in performing the power supply and the signal transmission is not restricted largely, and designing with large amount of freedom can be attained.

As described above, in the preferred embodiment of the present invention, the size of the analyzer is small. The analyzer has a modular structure. The setting data and the correction data are backed up when the body housing and the analysis measurement module are exchanged. Thereby, the analyzer can be used in the state before exchange without repeating a setting and a correction.

As used herein, the following directional terms "forward, rearward, above, downward, right, left, vertical, horizontal, below, and transverse" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, section or part of a device includes hardware and/or software that is constructed and/or programmed to carry out the desired function.

Moreover, terms that are expressed as "means-plus function" in the claims should include any structure that can be utilized to carry out the function of that part of the present invention.

The terms of degree such as "substantially," "about," "nearly", and "approximately" as used herein mean a reasonable amount of deviation of the modified term such that the end result is not significantly changed. For example, these terms can be construed as including a deviation of at least ±5 percents of the modified term if this deviation would not negate the meaning of the word it modifies.

The term "unit" is used to describe a component, section or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. An analyzer comprising:
a body housing having a first ID;
a first measurement module having a second ID that is different from the first ID, the first measurement module being releasably attachable to the body housing;
a first memory in the body housing, the first memory being configured to store the first ID, first setting data and first correction data;
a second memory in the first measurement module, the second memory being configured to store the second ID, second setting data and second correction data;
a first CPU in the body housing, the first CPU being configured to detect the first measurement module having the second ID; and
a first data transmission unit in the body housing, the first data transmission unit being configured to transmit the first setting data and the first correction data to the second memory.

2. The analyzer according to claim 1, further comprising:
a second CPU in the first measurement module, the second CPU being configured to detect the body housing having the first ID; and
a second data transmission unit in the first measurement module, the second data transmission unit being configured to transmit the second setting data and the second correction data to the first memory.

3. The analyzer according to claim 1, further comprising:
a display unit in a front side of the body housing, the display unit including a touch panel.

4. The analyzer according to claim 1, wherein the analyzer is configured to connect to an instrument panel room through a two-wire transmission path.

5. The analyzer according to claim 1, wherein the analyzer is configured to connect to an instrument panel room through a four-wire transmission path.

6. The analyzer according to claim 1, further comprising:
a second measurement module having a third ID that is different from the first ID and the second ID, the second measurement module being releasably attachable to the body housing;
a third memory in the second measurement module, the third memory being configured to store the third ID, third setting data and third correction data, and
wherein the first CPU is configured to detect the second measurement module having the third ID, and the first data transmission unit is configured to transmit the first setting data and the first correction data to the third memory.

7. The analyzer according to claim 6, further comprising:
a third CPU in the second measurement module, the third CPU being configured to detect the body housing having the first ID, and the first measurement module having the second ID; and
a third data transmission unit in the second measurement module, the third data transmission unit being configured to transmit the third setting data and the third correction data to the first memory and the second memory.

8. The analyzer according to claim 6, wherein the second CPU is configured to detect the second measurement module having the third ID, and the second data transmission unit is configured to transmit the second setting data and the second correction data to the third memory.

9. An analyzer comprising:
- a body housing having a first ID;
- a first measurement module having a second ID, the first measurement module being releasably attachable to the body housing;
- a first memory in the body housing, the first memory being configured to store the first ID, a third ID that is different from the first ID, first setting data and first correction data;
- a second memory in the first measurement module, the second memory being configured to store the second ID, a fourth ID that is different from the second ID, second setting data and second correction data;
- a first CPU in the body housing, the first CPU being configured to determine whether or not the second ID is different from the third ID; and
- a first data transmission unit in the body housing, the first data transmission unit being configured to transmit the first setting data and the first correction data to the second memory if the first CPU determines that the second ID is different from the third ID.

10. The analyzer according to claim 9, wherein the first memory is configured to store the second ID after the first setting data and the first correction data are transmitted to the second memory.

11. The analyzer according to claim 9, further comprising:
- a second CPU in the first measurement module, the second CPU being configured to determine whether or not the first ID is different from the fourth ID; and
- a second data transmission unit in the first measurement module, the second data transmission unit being configured to transmit the second setting data and the second correction data to the first memory if the second CPU determines that the first ID is different from the fourth ID.

12. The analyzer according to claim 9, further comprising:
- a display unit in a front side of the body housing, the display unit including a touch panel.

13. The analyzer according to claim 9, wherein the analyzer is configured to connect to an instrument panel room through a two-wire transmission path.

14. The analyzer according to claim 9, wherein the analyzer is configured to connect to an instrument panel room through a four-wire transmission path.

15. An analyzing method comprising:
- determining whether or not a first ID registered in a first memory of a body unit is different from a second ID allocated to a first measurement module; and
- transmitting first setting data and first correction data stored in the first memory to a second memory of the first measurement module if it is determined that the first ID is different from the second ID.

16. The analyzing method according to claim 15, further comprising:
- determining whether or not a third ID registered in the second memory is different from a fourth ID allocated to the body unit; and
- transmitting second setting data and second correction data stored in the second memory to the first memory if it is determined that the third ID is different from the fourth ID.

17. The analyzing method according to claim 15, further comprising:
- transmitting data to an instrument panel room through a two-wire transmission path.

18. The analyzing method according to claim 15, further comprising:
- transmitting data to an instrument panel room through a four-wire transmission path.

19. The analyzing method according to claim 15, further comprising:
- determining whether or not a fifth ID registered in the second memory is different from a sixth ID allocated to a second measurement module; and
- transmitting third setting data and third correction data stored in the second memory to a third memory of the second measurement module if it is determined that the fifth ID is different from the sixth ID.

20. The analyzing method according to claim 15, further comprising:
- registering the second ID in the first memory after the first setting data and the first correction data are transmitted to the second memory.

* * * * *